| United States Patent [19] | | [11] | 4,060,529 |
|---|---|---|---|
| Slejko | | [45] | Nov. 29, 1977 |

[54] POLYMERIZATION INHIBITORS FOR N-SUBSTITUTED AMINOALKYL ACRYLIC MONOMERS

[75] Inventor: Frank L. Slejko, Bristol, Pa.

[73] Assignee: Rohm and Haas Company, Philadelphia, Pa.

[21] Appl. No.: 612,401

[22] Filed: Sept. 11, 1975

Related U.S. Application Data

[63] Continuation-in-part of Ser. No. 477,126, June 6, 1974, abandoned.

[51] Int. Cl.$^2$ ............... C07D 263/06; C07C 103/133; C07D 265/06
[52] U.S. Cl. .......................... 260/307 FA; 260/513.5; 556/205; 544/171; 560/222; 526/312
[58] Field of Search ............. 260/307 FA, 486, 513.5; 556/405

[56] References Cited

FOREIGN PATENT DOCUMENTS

| 1,235,896 | 9/1967 | Germany | 556/205 |
| 39-25030 | 7/1964 | Japan | 556/205 |
| 43-29925 | 12/1968 | Japan | 556/205 |

*Primary Examiner*—Donald G. Daus
*Assistant Examiner*—D. B. Springer

[57] ABSTRACT

A method is disclosed for inhibiting the polymerization of N-substituted aminoalkyl acrylic monomers at ambient and above ambient temperatures such as during preparation, purification or storage of the monomers by adding thereto nabam, maneb, zineb, mancozeb, or a salt of tin (II), copper (I), manganese (II) or cobalt (II) in an amount effective to inhibit polymerization.

14 Claims, No Drawings

POLYMERIZATION INHIBITORS FOR N-SUBSTITUTED AMINOALKYL ACRYLIC MONOMERS

This application is a continuation-in-part of U.S. Ser. No. 477,126 filed June 6, 1974, now abandoned.

This invention relates to the use of an inhibitor system for preventing polymerization of N-substituted aminoalkyl acrylic monomers at ambient and above ambient temperatures, such as may occur in preparation, purification or storage of the acrylic monomers.

Acrylic ester monomers are well-known and their preparation has been amply disclosed in the literature and art. N-substituted aminoalkyl acrylic monomers are generally prepared by a transesterification reaction, typical examples of which are discussed in U.S. Pat. Nos. 2,744,884 and 3,714,234. Since the ester interchange of transesterification reaction is conducted in a temperature range of about 60° C. to about 150° C., polymerization of reaction product in the reaction zone due to heating above ambient temperatures is a persistent problem in monomer manufacture. Additionally, the almost universal method for purification of the crude acrylic ester monomers obtained by various processes involves the step of distillation. The problem encountered during this step which generally entails refluxing at elevated temperatures, is again the marked tendency for the monomer to polymerize. N-substituted aminoalkyl acrylic monomers tend to polymerize in the still pot as well as in the distillation columns. The heavy viscous polymer that forms in the still pot during distillation induces higher stress and strain on processing equipment, such as pumps, necessitating more frequent shutdowns. Likewise, polymerization on the plates of the distillation columns becomes so excessive as to force production shutdowns. These monomers are also subject to polymerization at ambient temperatures during prolonged storage in the absence of any inhibitors.

A variety of polymerization inhibitors have been developed and are known in the art. Among the most common are the phenol-based inhibitors such as the quinones, hydroquinones, nitrophenol as well as other organic and inorganic compounds. However, polymerization during distillation of N-substituted aminoalkyl acrylic monomers is still a problem due to the general ineffectiveness of the known inhibitors in suppressing the polymerization, with the resultant shutdowns discussed infra.

According to the present invention, an inhibitor is provided which is useful in inhibiting the polymerization of N-substituted aminoalkyl acrylic monomers. It is especially useful to prevent polymerization during the preparation of the monomers at elevated temperatures, as well as during distillation processes and during prolonged storage at ambient temperatures. N-substituted aminoalkyl acrylic monomers, the polymerization of which may be thus inhibited, include dimethylaminoethyl acrylate, diethylaminoethyl acrylate, dibutylaminoethyl acrylate, diethylaminopropyl acrylate, 2-dibutylaminopropyl acrylate, 3-dibutylaminopropyl acrylate, 2-morpholinoethyl acrylate, 2-[N-(2-hydroxyethyl)ethylamino]ethyl acrylate, t-butylaminoethyl methacrylate, dimethylaminoethyl methacrylate, 2-oxazolidinylethyl acrylate or methacrylate, and so forth. Such monomers may be generally represented by the formula:

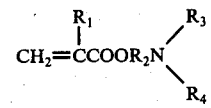

where $R_1$ is hydrogen or a methyl group, $R_2$ is a divalent alkylene radical of 1 to 5 carbon atoms, and $R_3$ is a hydrogen or an alkyl having 1 to 5 carbon atoms, $R_4$ is an alkyl having 1 to 5 carbon atoms, or $R_3$ and $R_4$ are taken together with the nitrogen atom to form a five or six membered saturated heterocyclic ring, optionally having at least one of the hetero atoms, N and O, in the ring.

The monomers are stabilized by contacting them with an amount of metallic salt, or complex in an amount effective to inhibit polymerization. The amount used may be as low as 0.1% by weight of the unsaturated monomer. As the salts and complexes are generally insoluble in the monomers no rigid upper limit on amount of inhibitor to be used can be spelled out, as even slurries can be used to inhibit polymerization. As a practical matter, about 4% by weight of the unsaturated monomer is a useful upper limit, as this amount is entirely sufficient to inhibit polymerization. The inhibitors of this invention are the salts of tin (II), copper (I), manganese (II), cobalt (II) as well as complexes and salts of manganese, sodium and zinc with ethylenebisdithiocarbamic acid. The useful salts include the halides, halogenates, sulfates, nitrates, chromates, phosphate as well as carboxylic acid salts such as acetates, citrates and so on. The useful zinc and maganese complexes and salts with ethylenebisdithiocarbamic acid include nabam, mancozeb, zineb and maneb. The stannous salts are preferred and the stannous halides and zineb are most preferred. Cuprous chloride is most preferred for use as an inhibitor during ambient temperature storage conditions.

As previously mentioned, the inhibitor of this invention may be employed to inhibit polymerization during the preparation of an N-substituted aminoalkyl acrylic monomers, such as by direct esterification or transesterification as well as during the purification of such acrylic monomers as by distillation. When the acrylic monomer is obtained in an aqueous medium, it may be extracted by means of an organic solvent from the aqueous solution and the solvent then stripped off in a distillation column. Alternatively, the acrylic monomer may be separated from the aqueous solution by distilling off the water. When inhibiting polymerization during a preparation step, as during a transesterification, the inhibitor is added directly to the reactants before or during the reaction. Likewise, the inhibitors can be contacted with the crude monomer in the still kettle of the distillation system prior to distillation. The inhibitors may also be added to the plates in the distillation column to prevent polymer formation therein. While the inhibitor of this invention does not always completely suppress the formation of the acrylic polymer, even if polymers do form, it is only after a considerably longer period of distillation than could be obtained without inhibitor. Additionally, purified monomers are effectively stabilized against polymerization during storage at ambient temperatures by the addition of the inhibitors of this invention.

Since the inhibitors are solids, and their vaporization points are higher than that of the monomers, the solid salts remain in the still pot with the advantage that the purified monomers collected overhead are free of inhibitor.

In the following examples, test are run showing the effect of these inhibitors on polymerization of t-butylaminoethyl methacrylate and 2-oxazolidinylethyl methacrylate under trial run conditions as well as conditions simulating actual full-scale production.

EXAMPLE I

Samples of crude t-butylaminoethyl methacrylate with different levels of stannous chloride are placed in 25 × 200 mm test tubes and heated in an oil bath over a range of temperatures. A control sample in run without stannous chloride. The results clearly demonstrate that even at low temperatures, crude t-butylaminoethyl methacrylate polymerizes without any inhibitor, while low levels of stannous chloride suppress polymerization even at higher temperatures.

TABLE I

| Temperature | | Control t-BAEMA | + 0.5% $SnCl_2$ | + 1.0% $SnCl_2$ |
|---|---|---|---|---|
| 80° C | Duration | 38.2 hrs. | 5 days | 5 days |
| | Appearance of Sample | Solid | Fluid | Fluid |
| 100° C | Duration | 91 hrs. | 91 hrs. | 91 hrs. |
| | Appearance of Sample | Solid (viscous after 24 hrs.) | Slightly viscous | Viscous |
| 130° C | Duration | 5 hrs. | 48 hrs. | 48 hrs. |
| | Appearance of Sample | Solid | Viscous | Less viscous than with 0.5% $SnCl_2$ |
| 150° C | Duration | 3 hrs. | 24 hrs. | 24 hrs. |
| | Appearance of Sample | Solid | Very viscous | Very viscous | t-BAEMA = tert-butylaminoethyl methacrylate

EXAMPLE II

Samples of previously distilled oxazolidinylethyl methacrylate to which are added different levels of stannous chloride are placed in 25 × 200 mm test tubes and heated in an oil bath to a temperature of 75° C. A control sample is run without stannous chloride. The results are summarized in Table II. Again, untreated samples show rapid onset of polymerization, whereas treated samples remain clear after 24 hours.

TABLE II

| Temperature | | Uninhibited OXEMA | + 0.4% $SnCl_2$ | + 1.2% $SnCl_2$ |
|---|---|---|---|---|
| 75° C | Duration | 4 hrs. | 24 hrs. | 24 hrs. |
| | Appearance of Sample | Viscous | no signs | no signs |

TABLE II-continued

| Temperature | | Uninhibited OXEMA | + 0.4% $SnCl_2$ | + 1.2% $SnCl_2$ |
|---|---|---|---|---|
| 75° C | Duration | 6 hrs. | of polymer | of polymer |
| | Appearance of Sample | Very thick and syrupy | | |

OXEMA = oxazolidinylethyl methacrylate

EXAMPLE III 350 gm samples of crude oxazolidinylethyl methacrylate (~50% methyl methacrylate, ~50% oxazolidinylethyl methacrylate) are placed in a 1-liter flask fitted with a thermometer, stirrer and fractionation column (10 plate Oldershaw). A sample is run without stannous chloride. The samples are heated with reflux, and stirred, at 115° C. until polymer forms. The results are summarized in Table III. Again, the time at which polymer appears is delayed by the addition of inhibitor.

TABLE III

| Inhibitor Added | Time For Polymer Formation |
|---|---|
| None | 4.5 hrs. |
| + 0.2% $SnCl_2$ | 5.5 hrs. |
| + 0.8% $SnCl_2$ | 11.0 hrs. |

EXAMPLE IV 3,000 gm batches of crude t-butylaminoethyl methacrylate are distilled from a 5-liter flask equipped with a stirrer, thermometer, a 5-plate Oldershaw fractionation column and a distillation head filled with automatic reflux control (75% forward). The crude t-butylaminoethyl methacrylate is composed of approximately the following:

| | |
|---|---|
| 7.3% | methyl methacrylate |
| 2.1% | t-butylaminoethanol |
| 79.2% | t-butylaminoethyl methacrylate |
| 5.1% | high boiling fraction |
| 6.3% | solids |
| 100.0% | |

A theoretical distillation recovery would be about 2,660 gm of low boiling fraction and product. The experiment is run with a control distillation having no inhibitor and a distillation with inhibitor. The distillation is carried out until no more product comes overhead. The results are summarized in Table IV. The results show that stannous chloride can provide much higher yields in product recovery over inhibitor-free recoveries.

TABLE IV

DISTILLATION OF CRUDE t-BAEMA

| Crude t-BAEMA | | | | | Crude t-BAEMA + 1% $SnCl_2$ | | | | |
|---|---|---|---|---|---|---|---|---|---|
| Time (Hrs) | Pot (C°) | Head (C°) | Pressure (mm Hg) | Total Amount Collected | Time (Hrs) | Pot (C°) | Head (C°) | Pressure (mm Hg) | Total Amount Collected |
| 0 | 89 | 30 | 55 | 1st drop | 0 | 87 | 30 | 55 | 1st drop |
| 2.5 | 93.5 | 67 | 7 | 68 gm | 2.0 | 97 | 84 | 8 | 123 gm |
| 5.5 | 99 | 84 | 7 | 313 gm | 6.5 | 100 | 88 | 8 | 663 gm |
| 12.0 | 101 | 86 | 7 | 874 gm | 14.0 | 103 | 90 | 8 | 1348 gm |
| 18.5 | 101 | 86 | 7 | 1485 gm | 21.5 | 104 | 89 | 8 | 2093 gm |
| 25.0 | 102 | 87 | 7 | 1743 gm | 27.5 | 129 | 84 | 8 | 2410 gm |
| 31.5 | 109 | 86 | 7 | 2317 gm | 29.0 | 138 | 82 | 8 | 2513 gm |
| Yield = 87% | | | | | Yield = 94% | | | | | t-BAEMA = t-butylaminoethyl methacrylate

EXAMPLE V

Samples of previously distilled oxazolidinylethyl methacrylate, to which are added various inhibitors at the level of 1% per weight of monomer, are placed in 25 × 200 mm test tubes and heated in an oil bath to a temperature of 75° C. A control sample in run without any inhibitor. The results are summarized in Table V. Untreated samples show rapid onset of polymerization while some treated samples remain clear after 96 hours and others show polymer onset only after a long period of heating.

TABLE V

| INHIBITOR | ONSET TIME (hrs) | APPEARANCE |
| --- | --- | --- |
| None | 6–8 | Polymer |
| $MnCl_2$ | 22.0 | Polymer |
| $Co(NO_3)_2$ | 27.0 | Polymer |
| CuCl | 96.0[1] | No Polymer |
| $SnCl_2$ | 96.0[1] | No Polymer |

[1]Sample heated for this length of time without showing polymer onset.

EXAMPLE VI

Samples of previously distilled oxazolidinylethyl methacrylate, to which are added various inhibitors at the level of 1% per weight of monomer are heated in 25 × 200 mm test tubes to a temperature of 75° C. under nitrogen sparge. A control sample is run without any inhibitor. The results are summarized in Table VI.

TABLE VI

| INHIBITOR | ONSET TIME (hrs) | APPEARANCE |
| --- | --- | --- |
| None | 1 hour | Polymer |
| $ZnCl_2$ | 1 hour | Polymer |
| Zineb | 79.0 | Polymer |
| Mancozeb | 96.0[2] | No Polymer |
| Mancozeb[1] | 110.0 | Polymer |

[1]Different sample of mancozeb from previous sample.
[2]Sample heated for this length of time without showing polymer onset.

EXAMPLE VII

Samples of distilled oxazolidinylethyl methacrylate are stored at ambient temperature with and without inhibitor to determine the stabilizing effect of the inhibitors. The monomer is stored in capped bottles at a temperature of about 20° C. The results are summarized in Table VII. It is apparent from the results that while stannous chloride is extremely effective in preventing polymerization in above ambient temperature conditions, it is definitely unacceptable in ambient temperature monomer storage conditions.

TABLE VII

| INHIBITOR | ONSET TIME (days) | APPEARANCE |
| --- | --- | --- |
| None | 4 | Solid |
| 1% $SnCl_2$ | 1 | Solid |
| 1% CuCl | 17[1] | Fluid (no polymer) |

[1]Sample stored this long without showing polymer onset.

I claim:

1. A method for inhibiting the polymerization of acrylic monomers having the formula:

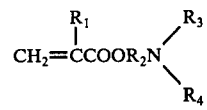

where
R$_1$ is hydrogen or methyl,
R$_2$ is a divalent alkylene radical of 1 to 5 carbon atoms, and
R$_3$ is a hydrogen or an alkyl having 1 to 5 carbon atoms,
R$_4$ is an alkyl having 1 to 5 carbon atoms, or
R$_3$ and R$_4$ are taken together with the nitrogen atom to form a five or six membered saturated heterocyclic ring, optionally having at least one of the hetero atoms, N and O, in the ring,
at ambient and above ambient temperatures, said method comprising contacting said monomers with an amount of nabam, mancozeb, maneb, zineb, or a halide, halogenate, sulfate, nitrate, chromate, phosphate or carboxylate of tin (II), copper (I), manganese (II) or cobalt (II), effective to inhibit the polymerization of the monomers during the preparation, purification or storage of said monomers.

2. The method of claim 1, wherein the preparation of the monomers is by a transesterification reaction.

3. The method of claim 1 wherein the preparation of the monomer is by a direct esterification reaction.

4. The method of claim 1, wherein the purification of the monomers is by distillation.

5. The method of claim 1, wherein said monomer is t-butylaminoethyl methacrylate.

6. The method of claim 1, wherein said monomer is dimethylaminoethyl methacrylate.

7. The method of claim 1, wherein said monomer is 2-oxazolidinylethyl methacrylate.

8. The method of claim 1, wherein the inhibitor is a stannous halide.

9. The method of claim 8, wherein the stannous halide is stannous chloride.

10. The method of claim 1, wherein the inhibitor is zineb used during purification of the monomers by distillation.

11. The method of claim 1, wherein the inhibitor is cuprous chloride used during storage of 2-oxazolidinylethyl methacrylate.

12. The method of claim 1, wherein the inhibitors are used in an amount of 0.1 to 4% by weight based on weight of said monomer.

13. The method of claim 1, wherein inhibitors are used in an amount of 0.4 to 2% by weight based on weight of said monomer.

14. The method of claim 4, wherein the inhibitor is added to the distillation column and to the still kettle prior to or during distillation.

* * * * *